United States Patent

Michurov et al().

[11] 4,113,976
[45] Sep. 12, 1978

[54] METHOD OF PREPARING 2,6-DI-TERT.BUTYLPHENOL

[76] Inventors: Jury Ivanovich Michurov, prospekt Lenina, 13, kv. 4; Boris Izrailevich Pantukh, ulitsa Khudaiberdina, 162, kv. 89, both of Bashkirskaya ASSR; Valerian Mikhailovich Sobolev, Maxima Gorkogo, 48/50, kv. 185, Moscow; Grigory Iosifovich Rutman, ulitsa Revoljutsionnaya, 7, kv. 6, Bashkirskaya ASSR; Igor Jurievich Logutov, ulitsa Druzhby, 47, kv. 50, Bashkirskaya ASSR; Vladimir Romanovich Dolidze, ulitsa Kurchatova, 30, kv. 8, Bashkirskaya ASSR, all of U.S.S.R.

[21] Appl. No.: 788,590

[22] Filed: Apr. 18, 1977

[51] Int. Cl.$^2$ ............................................. C07C 39/02
[52] U.S. Cl. ............................. 568/789; 260/448 AD
[58] Field of Search ............... 260/624 C, 624 R, 626, 260/624 L, 448 AD; 252/463, 431 R

[56] References Cited

U.S. PATENT DOCUMENTS 3,766,276  10/1973  Goddard 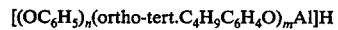 260/624 R

Primary Examiner—James O. Thomas, Jr.
Assistant Examiner—Werren B. Lone
Attorney, Agent, or Firm—Lackenbach, Lilling & Siegel

[57] ABSTRACT

A method of preparing 2,6-di-tert.butylphenol comprises alkylation of phenol with isobutylene at a temperature within the range of from 100° to 110° C in the presence, as a catalyst, of phenyloxyorthotertbutyl-phenoxyhydroaluminum acid of the formula:

$$[(OC_6H_5)_n(\text{ortho-tert.}C_4H_9C_6H_4O)_m Al]H$$

wherein
$n = 1$ to 3;

$m = 1$ to 3;

$n + m = 4$.

The method of the present invention makes it possible to increase the product yield to 80% by weight and to conduct the process under atmospheric pressure.

1 Claim, No Drawings

METHOD OF PREPARING 2,6-DI-TERT.BUTYLPHENOL

The present invention relates to the art of petrochemical synthesis and, more specifically, to substituted phenols, in particular, it relates to methods of preparing 2,6-ditert.butylphenol.

2,6-di-tertbutylphenol is useful in the field of organic synthesis and, in particular, for the production of phenolic stabilizers employed for stabilization of synthetic rubber, plastics, synthetic fibres. Phenolic stabilizers such as 4-methyl-2,6-ditertbutylphenol (ionol) are also useful as antioxidant additive for oils, fuels and other petroleum products.

BACKGROUND OF THE INVENTION

A prior art process for the preparation of 2,6-di-tert.butylphenol comprises alkylation of phenol with an olefin in presence of aluminum phenolate.

This prior art method makes it possible to obtain 2,6-di-tertbutylphenol with a yield of 75–87% by weight, while 22–25% by weight constitute by-products, namely para-tert.butylphenol, 2,4-di-tertbutylphenol and tri-tert.butylphenol.

Known in the art is a method of preparing 2,6-ditert.butylphenol by alkylation of phenol with isobutylene in the presence of aluminium chloride under the pressure of 70 atm. (cf. U.S. Pat. No. 2,923,745). In this method the product yield is 56 to 60% by weight.

Also known is another method of preparing 2,6-di-tert.butylphenol by alkylation of phenol with isobutylene in the presence of aluminum phenolate at temperature of 150° C under a pressure of from 45 to 50 atm. The yield of 2,6-ditertbutylphenol is 76–79% by weight. Despite the high product yield this method has disadvantages which reside in the necessity of employing sophisticated process equipment due to the use of high pressures.

It is an object of the present invention to improve the method of preparing 2,6-di-tert.butylphenol to increase the product yield with a simultaneous simplification of the process technology.

SUMMARY OF THE INVENTION

The object of the present invention is accomplished by a method of preparing 2,6-di-tert.butylphenol which comprises alkylation of phenol with isobutylene at a temperature of 100° to 110° C in the presence of phenyloxyorthotertbutylphenoxyhydroaluminum acid, as a catalyst, having the formula:

$$(OC_6H_5)_n(\text{ortho-tert.}C_4H_9C_6H_4O)_m Al\ H,$$

wherein $n = 1$ to 3, $m = 1$ to 3;

$n + m = 4$.

This catalyst makes it possible to perform the process under mild conditions, i.e. under atmospheric pressure, and to increase the product selectivity relative to the desired product up to 90–95% and, consequently, the product yield up to 80% by weight.

DETAILED DESCRIPTION OF THE PROCESS

Phenol and the above-mentioned catalyst are charged into a reactor; the mixture is heated to 100°–110° C and isobutylene is passed thereinto for 8 hours. The resulting alkylate is subjected to a vacuum-rectification. After recrystallization of the product from aliphatic hydrocarbons, a 100% pure 2,6-di-tertbutylphenol is obtained.

The starting alkylation catalyst can be prepared by reacting aluminum phenolate with ortho-tertbutylphenol resulting from the alkylate rectification. The catalyst amount in the alkylation process can be varied within the range of from 0.5 to 1% by weight as calculated for aluminum.

The process is conducted, as it has been mentioned hereinbefore, at a temperature within the range of from 100° to 110° C. Alkylation at a temperature below 100° C results in a decreased yield of 2,6-di-tertbutylphenol, whereas alkylation at a temperature above 110° C results in undesirable changes in composition of alkylphenols and an increased amount of the by-products.

For a better understanding of the present invention some specific Examples are given hereinbelow by way of illustration.

EXAMPLE 1

74.98 g of a catalyst having the composition corresponding to the formula [$(C_6H_5O)_2$(ortho-tert.$C_4H_9C_6H_4O)_2$Al]H are added into a mixture of 172.4 g of phenol and 156 g of ortho-tert.butylphenol. The mixture is heated to a temperature of 110° C and isobutylene is passed therethrough for 8 hours to give 697 g of an alkylate with the following composition, percent by weight: phenol 0.2, ortho-tertbutylphenol 10.5; 2,6-ditertbutylphenol 80.1; 2,4-ditertbutylphenol 0.2; 2,4,6-tri-tertbutylphenol 9. The alkylate is exempted of the catalyst by hydrolysis with water and subjected to rectification under vacuum. The recovered 2,6-di-tertbutylphenol melts at 35° C. The product yield is 80.1% by weight of the theoretical value. To obtain 2,6-ditertbutylphenol of a 100% purity grade, it is subjected to rectification and recrystallization from normal-structure hydrocarbons. Purity of the product, according to the data of gas-liquid chromatography (GLC) is 100%; melting point is 35.2° C.

EXAMPLE 2

25.0 g of a catalyst of the formula: [$(OC_6H_5)_3$(ortho-tert.$C_4H_9C_4O)_1$Al]H are mixed with 100 g of phenol and 40 g of ortho-tertbutylphenol. The mixture is heated to a temperature of 105° C and isobutylene is passed thereinto for 8 hours. The resulting alkylate is exempted of the catalyst to give a mixture of alkylphenols of the following composition, percent by weight: phenol 0.6; ortho-tertbutylphenol 16.2; 2,6-di-tertbutylphenol 76; 2,4-di-tertbutylphenol 0.2; 2,4,6-tri-tertbutylphenol 5. Selectivity is 94.47%.

EXAMPLE 3

37.49 g of a catalyst of the formula: [$(OC_6H_5)_1$(ortho-tert$C_4H_9C_6H_4O)_3$Al]H are mixed with 86.2 g of phenol. The mixture is heated to a temperature of 110° C and isobutylene is passed therethrough for 8 hours. The catalyst is then removed from the resulting alkylate to give a mixture of alkylphenols having the following composition, percent by weight: phenol 0.2; ortho-tertbutylphenol 10.6; 2,6-ditertbutylphenol 80.0; 2,4di-tertbutylphenol 0.4; 2,4,6-tri-tertbutylphenol 9%. Selectivity is 90.5%.

EXAMPLE 4

This Example illustrates the catalyst preparation (the composition is the same as in Example 1 hereinbefore).

30.6 g aluminum phenolate dissolved in an aliphatic solvent (such as heptane) are mixed with 30 g of ortho-tertbutylphenol. The mixture is stirred for 1 hour at room temperature; after the removal of the solvent there are obtained 51.2 g of a catalyst having the following composition:

$$[(OC_6H_5)_2(\text{ortho-tert}C_4H_9C_6H_4O)_2Al]H.$$

What is claimed is:

1. A method of preparing 2,6-di-tertbutylphenol comprising alkylation of phenol with isobutylene at a temperature of from 100° to 110° C in the presence of 0.5 to 1% by weight of phenoloxyorthotertbutylphenoxyhydroaluminum acid having the formula:

$$[(OC_6H_5)_n(\text{ortho-tert.}C_4H_9C_6H_4O)_m Al]H$$

wherein $n = 1$ to 3, $m = 1$ to 3; $n+m = 4$, to form an alkylate, hydrolyzing said catalyst; vacuum rectifying the alkylate; and recovering 2,6-di-tertbutylphenol by recrystallization.